United States Patent
Zhu et al.

(10) Patent No.: US 9,506,875 B2
(45) Date of Patent: Nov. 29, 2016

(54) DETECTION-EVALUATION METHOD AND DEVICE FOR MOIRÉ PATTERN

(71) Applicant: BOE TECHNOLOGY GROUP CO., LTD., Beijing (CN)

(72) Inventors: Jinye Zhu, Beijing (CN); Wei Wei, Beijing (CN); Naifu Wu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 22 days.

(21) Appl. No.: 14/415,953

(22) PCT Filed: Apr. 30, 2014

(86) PCT No.: PCT/CN2014/076614
§ 371 (c)(1),
(2) Date: Jan. 20, 2015

(87) PCT Pub. No.: WO2015/100896
PCT Pub. Date: Jul. 9, 2015

(65) Prior Publication Data
US 2015/0377798 A1    Dec. 31, 2015

(30) Foreign Application Priority Data

Dec. 30, 2013 (CN) .......................... 2013 1 0744422

(51) Int. Cl.
*G01B 11/24* (2006.01)
*G01N 21/956* (2006.01)
*G02F 1/00* (2006.01)

(52) U.S. Cl.
CPC ............... *G01N 21/956* (2013.01); *G02F 1/00* (2013.01)

(58) Field of Classification Search
CPC combination set(s) only.
See application file for complete search history.

(56) References Cited

U.S. PATENT DOCUMENTS

2012/0133938 A1* 5/2012 Deckers ............. G03F 7/70483
356/388

FOREIGN PATENT DOCUMENTS

| CN | 1690678 | | 11/2005 |
|---|---|---|---|
| CN | 101451909 | A | 6/2009 |
| CN | 102692207 | A | 9/2012 |
| CN | 102724545 | A | 10/2012 |
| CN | 103414911 | A | 11/2013 |
| CN | 103414912 | A | 11/2013 |

(Continued)

OTHER PUBLICATIONS

1st Office Action issued in Chinese application No. 201310744422.5 issued Jul. 29, 2015.
Form PCT/ISA/237 issued in International application No. PCT/CN2014/076614 mailed Oct. 9, 2014.
International Search Report dated Apr. 30, 2014 from application No. PCT/CN2014/076614.

(Continued)

*Primary Examiner* — Tri T Ton
(74) *Attorney, Agent, or Firm* — Nath, Goldberg & Meyer; Joshua B. Goldberg; Christopher Thomas

(57) ABSTRACT

The present invention relates to the field of display technology and discloses a detection-evaluation method for moiré pattern, comprising steps of: S1, detecting luminances at a plurality of continuous positions in a predetermined region of a display panel which is displaying a full white picture, so as to obtain a luminance curve; and S2, judging whether a graphics including peaks and valleys exists in the luminance curve, if the graphics exists, determining that the moiré pattern exists. The present invention further discloses a detection-evaluation device for moiré pattern. The present invention realizes an effective and accurate detection for moiré pattern, and overcomes shortcomings in visual inspection.

14 Claims, 4 Drawing Sheets

(56) References Cited

FOREIGN PATENT DOCUMENTS

| | | | |
|---|---|---|---|
| CN | 103645036 A | | 3/2014 |
| JP | 2001201459 A | | 7/2001 |
| JP | 2002350361 A | | 12/2002 |
| JP | 2005-24503 A | | 1/2005 |
| JP | 2009156857 A | * | 7/2009 ............ G01M 11/00 |
| JP | 2011-47808 A | | 3/2011 |
| TW | 201024702 A | | 7/2010 |

OTHER PUBLICATIONS

Liang, Cho-Liang "Measurement on the Modulation Depth of Moire and Spot Size"; CRT R&D Division, TECO Information Systems Co., Ltd.; Kuang-In,Taoyuan, Taiwan, R.O.C.; ASID; 1999; pp. 261-264.

Notification of the Second Office Action dated Mar. 15, 2016 corresponding to Chinese application No. 201310744422.5.

Notification of the Third Office Action dated Sep. 6, 2016 corresponding to Chinese application No. 201310744422.5.

* cited by examiner

DETECTION-EVALUATION METHOD AND DEVICE FOR MOIRÉ PATTERN

This is a National Phase Application filed under 35 U.S.C. 371 as a national stage of PCT/CN2014/076614, filed Apr. 30, 2014, an application claiming the benefit of Chinese Application No. 201310744422.5, filed Dec. 30, 2013, the content of each of which is hereby incorporated by reference in its entirety.

FIELD OF THE INVENTION

The present invention relates to the field of display technology, and particularly relates to a detection-evaluation method and a detection-evaluation device for moiré pattern.

BACKGROUND OF THE INVENTION

In the display field, moiré pattern represents alternate bright and dark stripes. At present, as limitations in the development of display technology, appearance of moiré pattern is very common when watching a naked eye 3D image. For this reason, detection and evaluation of severity of moiré pattern has become a critical index in evaluation of a 3D display panel during manufacturing a 3D display panel.

Currently, existing moiré pattern detection methods are generally based on visual inspection, and if alternate bright and dark stripes can be observed, it can be determined that there exists moiré pattern. However, occasionally, moiré pattern is very thin, and thus it is not easily inspected by eyes. Moreover, it cannot be assured to perform visual inspection at every angle (that is, angles within the coverage of view angle of display), and results of inspections from different inspectors after visual inspecting the same display panel may be different or contrary. In a word, moiré pattern cannot be effectively detected by using the existing moiré pattern detection methods.

SUMMARY OF THE INVENTION

I. Problem to be Solved

The problem to be solved in the present invention is how to effectively detect and evaluate moiré pattern.

II. Technical Solutions

To solve the above problem, the present invention provides a detection-evaluation method for moiré pattern, including the following steps:

step S1, detecting luminances at a plurality of continuous positions in a predetermined region of a display panel which is displaying a full white picture, so as to obtain a luminance curve; and step S2, judging whether a graphics including peaks and valleys exists in the luminance curve, and if the graphics exists, determining the existence of moiré pattern.

For example, in the step S1, the luminances at the plurality of continuous positions are detected vertically in a rectilinear direction parallel to the display panel.

For example, in the step S1, the luminances at a plurality of horizontal continuous positions are detected at a reference point, so as to obtain a horizontal luminance curve, and/or the luminances at a plurality of vertical continuous positions are detected at a reference point, so as to obtain a vertical luminance curve.

For example, the detection in the step S1 is performed by using a luminance meter or a CCD.

For example, after the step S2, the method further comprises:

calculating a luminance ratio between every adjacent peak and valley to obtain several peak-to-valley ratios $P_i$;

calculating an average deviation degree S, with respect to 1, of the peak-to-valley ratios to evaluate the moiré pattern according to the following formula:

$$S = \sqrt{\frac{1}{n-1}\sum_{i=1}^{n}(P_i-1)^2}$$

where n is the number of the peak-to-valley ratios and $P_i$ is the i-th peak-to-valley ratio.

For example, after the step S2, the method further comprises:

calculating a luminance ratio between adjacent peak and valley to obtain several peak-to-valley ratios $P_i$;

calculating a deviation degree $s_i=P_i-1$, with respect to 1, of every peak-to-valley ratio, wherein $P_i$ is the i-th peak-to-valley ratio; and generating a curve with using angles of detections as abscissa and using $s_i$ as ordinates so as to evaluate the moiré pattern.

The present invention further provides a detection-evaluation device for moiré pattern, including:

a luminance detection unit which is used for detecting luminances at a plurality of continuous positions in a predetermined region of a display panel which is displaying a full white picture, so as to obtain a luminance curve; and a curve judgment unit which is used for judging whether a graphics including peaks and valleys exists in the luminance curve, and if the graphics exists, the curve judgment unit determines that there exists moiré pattern.

For example, the detection-evaluation device for moiré pattern further comprises a linear guide rail which is parallel to the display panel, wherein the luminance detection unit moves along the linear guide rail.

For example, the luminance detection unit vertically detects a luminance at each of the continuous positions to obtain a luminance curve.

For example, the detection-evaluation device for moiré pattern further comprises a support which is used for fixing the luminance detection unit and enabling the luminance detection unit to rotate around a fixed point, such that luminances at a plurality of horizontal continuous positions are detected by the luminance detection unit, so as to obtain a horizontal luminance curve, and/or luminances at a plurality of vertical continuous positions are detected by the luminance detection unit, so as to obtain a vertical luminance curve.

For example, the luminance detection unit includes a luminance meter or a CCD.

For example, the detection-evaluation device for moiré pattern further comprises:

a peak-to-valley ratio calculation unit which is used for calculating a luminance ratio between adjacent peak and valley to obtain several peak-to-valley ratios Pi; and an average deviation degree calculation unit which is used for calculating an average deviation degree S, with respect to 1, of the peak-to-valley ratios to evaluate the moiré pattern according to the following formula:

$$S = \sqrt{\frac{1}{n-1}\sum_{i=1}^{n}(P_i-1)^2}$$

where n is the number of the peak-to-valley ratios and $P_i$ is the i-th peak-to-valley ratio.

For example, the detection-evaluation device for moiré pattern further comprises:

a peak-to-valley ratio calculation unit which is used for calculating a luminance ratio between adjacent peak and valley to obtain several peak-to-valley ratios $P_i$;

an deviation degree calculation unit which is used for calculating a deviation degree $s_i=P_i-1$, with respect to 1, of every peak-to-valley ratio, wherein $P_i$ is the i-th peak-to-valley ratio; and a curve generation unit which is used for generating a curve with using angles of detections as abscissa and using $s_i$ as ordinates so as to evaluate moiré pattern.

III. Advantageous Effects

In the present invention, a luminance curve is obtained by detecting the luminances of the display panel (which may be a virtual luminance curve detected therein), whether a graphics including peaks and valleys exists in the luminance curve is judged, and if the graphics exists, existence of moiré pattern is determined, so that an effective and accurate detection for moiré pattern can be realized, and thus shortcomings in visual inspection are overcome.

DETAILED DESCRIPTION OF THE EMBODIMENTS

Hereinafter, specific implementations of the present invention will be further described in detail in conjunction with accompanying drawings and embodiments. The following embodiments are used for illustrating the present invention, but not to limit the scope of the present invention.

Figure 1:
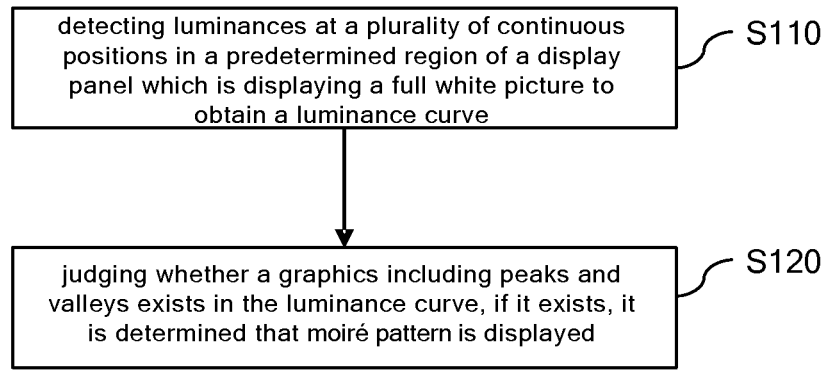
FIG. 1 is a flowchart of a detection-evaluation method for moiré pattern, according to an embodiment of the present invention.

As shown in FIG. 1, in an embodiment of the present invention, the detection-evaluation method for moiré pattern includes steps S110 and S120.

Step S110, detecting luminances at a plurality of continuous positions in a predetermined region of a display panel which is displaying a full white picture to obtain a luminance curve (which may also be a luminance curve virtually existed in the device). This step may specifically comprise:

First, the display panel is made to display a full white picture, then luminances at a plurality of continuous positions in a predetermined region of a display panel which is displaying the full white picture are detected by using a luminance meter or a CCD (Charge-coupled Device), and a luminance curve is generated.

In such a case, the predetermined region may be whole of the display panel, or a part of the display panel, such as a central region, or a bar region from one side to the opposite side of the display panel, which may be decided as desired. For example, when a CCD is used, whole of the display panel or a central region thereof may be photographed so as to obtain a luminance curve. When photographing, the CCD may be parallel to the display panel or has a certain angle (as long as within the coverage of the view angle of the display panel) with respect to the display panel. Furthermore, a plurality of luminance curves are generated after photographing at a plurality of angles so as to comprehensively detect and evaluate the moiré pattern of the display panel.

The luminance meter generally collects the luminance of a point region only. Accordingly, in a case of using the luminance meter, the luminances at a plurality of continuous positions in a predetermined region of a display panel which is displaying a full white picture may be continuously detected, starting from one position on the display panel. An example of detecting moiré pattern by using luminance meter will be described as following.

Figure 2:
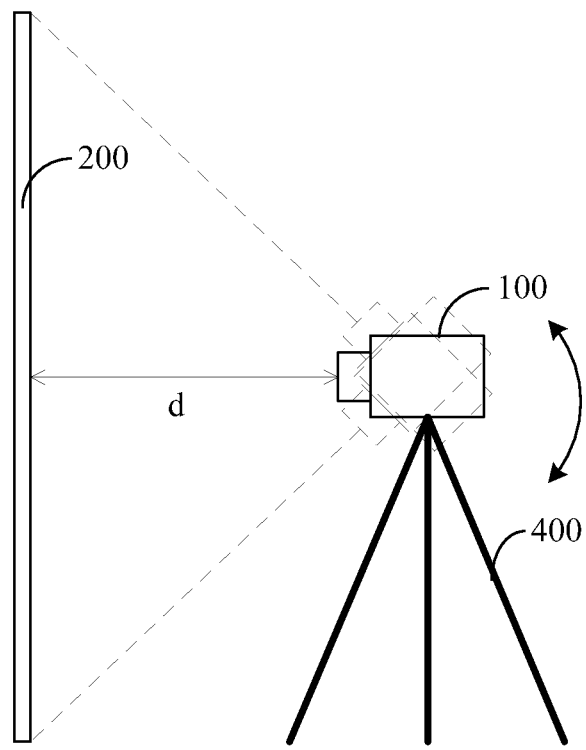
FIG. 2 is a schematic diagram illustrating detection of luminances of a display panel in a rotated manner.
Figure 3:
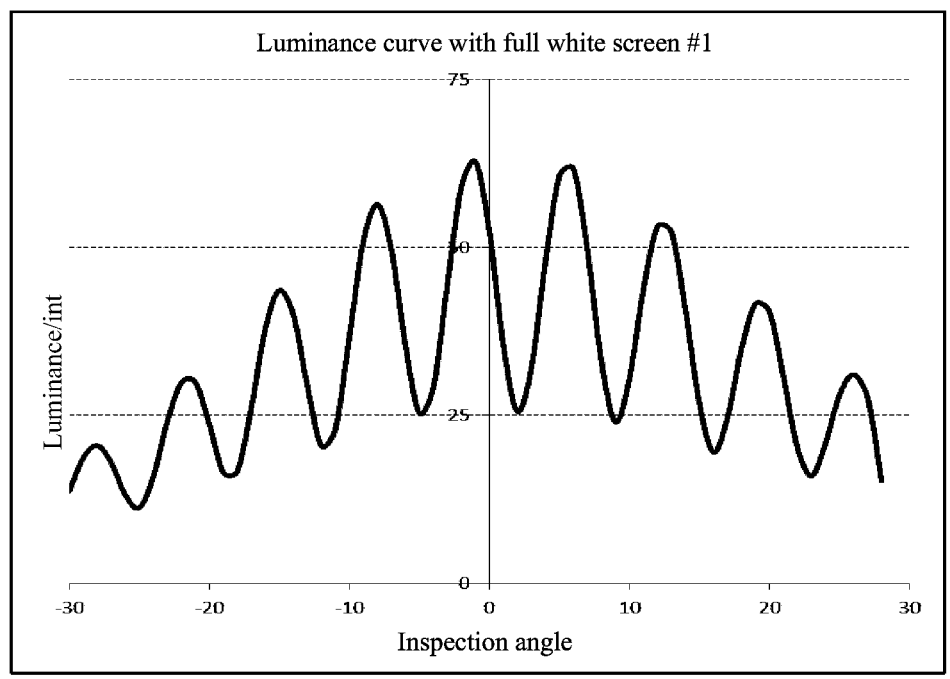
FIG. 3 is a graph of luminance curve obtained in the manner shown in FIG. 2.

As shown in FIG. 2, in order to verify viewing conditions at various view angles (that is, angles within the coverage of view angle of the display panel), the luminance meter 100, which is rotatable around a fixed point, is fixed on a support 400, so as to rotate during detection and continuously detect the luminances at a plurality of different continuous positions on the display panel 200. Specifically, the luminances at the plurality of different continuous positions on the display panel 200 which is displaying a full white picture may be detected through horizontally rotating the luminance meter at various detecting angles (each of which is an included angle between the detecting line and the normal of the display panel, and which may also be called inspection angles, the detecting line is a connection line between the detection head of the luminance meter and the detecting point on the display panel) corresponding to the plurality of different continuous positions horizontally arranged on the display panel 200, and a horizontal luminance curve is obtained. Then whether the moiré pattern exists may be judged based on the horizontal luminance curve. Also, the luminances at a plurality of different continuous positions on the display panel 200 which is displaying a full white picture may be detected at various detecting angles corresponding to the plurality of different continuous positions vertically arranged on the display panel 200 (that is, in a manner of rotating the luminance meter in a vertical plane), and a vertical luminance curve is obtained. Then whether the moiré pattern exists may be judged based on the vertical luminance curve. In addition, it is possible to detect horizontally and vertically to obtain two luminance curves. Of course, an oblique detection is also possible, thus a plurality of luminance curves may be obtained to perform a comprehensive detection and evaluation. The distance d between the luminance meter 100 and the display panel is adjusted, so that luminance detections for different coverage of view angle may be simulated. In such a case, the smaller d is, the larger the coverage of view angle is, and the larger d is, the smaller the coverage of view angle is. As shown in FIG. 3, a schematic diagram of luminance curve detected by rotating the luminance meter is illustrated, wherein the horizontal axis represents angle of detection, and the vertical axis represents luminance. The angles of detections on the horizontal axis represent included angles between the detecting lines and a vertical normal plane of the display panel, FIG. 3 shows a luminance curve wherein the inspection angles with respect to the normal are −30°~30°.

Figure 4:
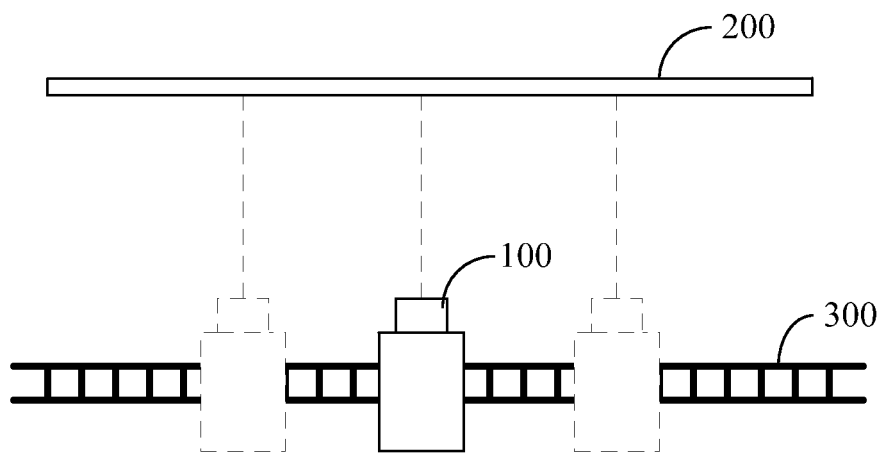
FIG. 4 is a schematic diagram illustrating detection of luminances of a display panel in a manner of translating in a straight line.
Figure 5:
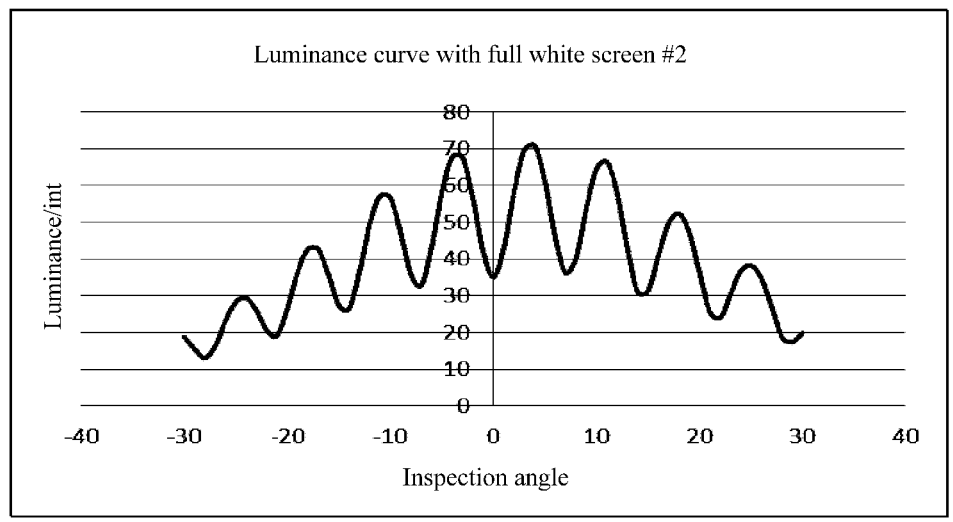
FIG. 5 is a graph of luminance curve obtained in the manner shown in FIG. 4.

As shown in FIG. 4, detection of luminance may be performed by translating the luminance meter 100 along a guide rail 300, wherein the luminance meter 100 is always perpendicular to the display panel 200. Preferably, the guide rail 300 is parallel to the display panel 200. The obtained luminance curve is shown in FIG. 5, wherein the horizontal axis represents moving distance of detecting point on the display panel.

It possible to detect the luminance by a CCD through using the above guide rail 300 and support 400 as moving carriers.

Step 120, judging whether a graphics including peaks and valleys exists in the luminance curve, and if the graphics exists, it is determined that moiré pattern is displayed. Moiré pattern is alternate bright and dark stripes, in a case where moiré pattern is displayed, a graphics including peaks and valleys must be existed in the luminance curve and in a case where moiré pattern is not displayed, the luminance curve is an uniform arc with high portion in middle and low portions in both ends (in a case of no moiré pattern and having uniform luminance, the luminance curve is a straight line, and if the luminance is not uniform, the luminance curve is a uniformly changed parabola). The luminance meter or the CCD may judge whether the pattern including peaks and valleys exists depending on values of the luminances detected by itself.

In view of above, whether the moiré pattern is displayed may be judged through determining whether the pattern including peaks and valleys exists in the luminance curve. Moreover, according to the positions of peaks and valleys in the luminance curve, the inspection angle at which the moiré pattern can be inspected and the approximate region in the display panel in which the moiré pattern exists can be determined. In comparison with the conventional visual inspection, an effective and accurate detection for moiré pattern can be realized.

In order to further analyse the moiré pattern so as to evaluate the severity of the moiré pattern displayed on the display panel, after the step S120, the method further comprises:

calculating a luminance ratio between adjacent peak and valley to obtain several peak-to-valley ratios $P_i$;

calculating an average deviation degree S, with respect to 1, of the peak-to-valley ratios to evaluate the moiré pattern according to the following formula:

$$S = \sqrt{\frac{1}{n-1}\sum_{i=1}^{n}(P_i-1)^2}$$

where n is the number of the peak-to-valley ratios and $P_i$ is the i-th peak-to-valley ratio. The larger the average deviation degree S is, the larger the deviation degree is, that is, the larger the difference between the peak-to-valley ratio in a case of the moiré pattern exists and that in an ideal case of no moiré pattern is, the worse the moiré pattern is, and thus the worse the quality of the display is.

Figure 6:
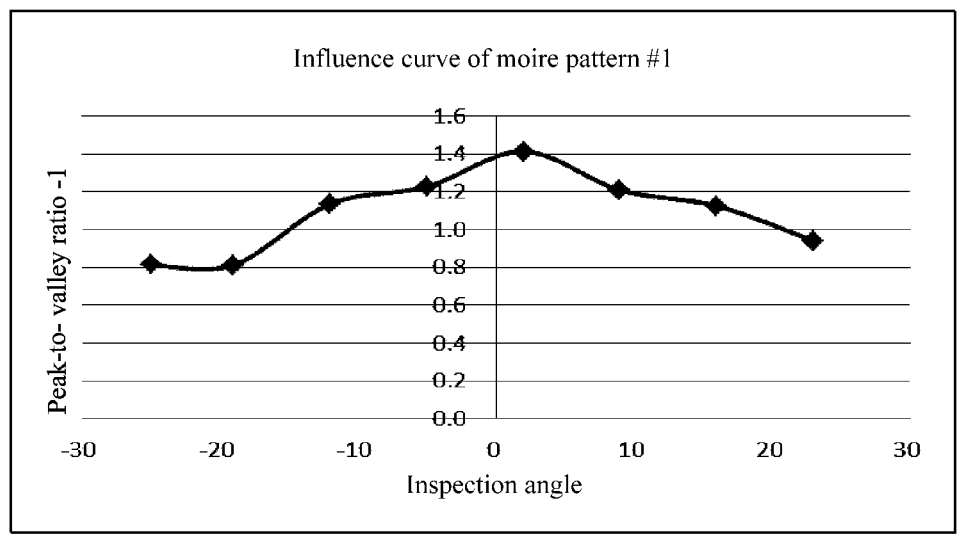
FIG. 6 is a graph illustrating influence curve of moiré pattern obtained based on the luminance curve shown in FIG. 3.
Figure 7:
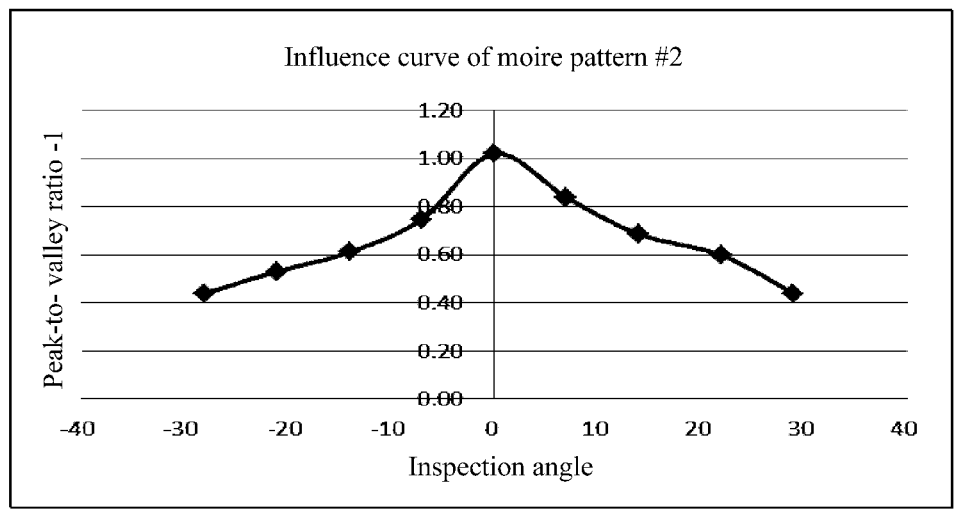
FIG. 7 is a graph illustrating influence curve of moiré pattern obtained based on the luminance curve shown in FIG. 5.

Furthermore, in order to exhibit the severity of the moiré pattern displayed on the display panel more intuitively, the severity of the moiré pattern may also be judged in another manner, that is, after the step S2, the method may further comprise:

calculating a luminance ratio between adjacent peak and valley to obtain several peak-to-valley ratios $P_i$;

calculating a deviation degree $s_i=P_i-1$, with respect to 1, of every peak-to-valley ratio; and generating a curve with using angles of detections or moving distances of detecting points on the display panel as abscissa and using $s_i$ as ordinates. FIG. 6 and FIG. 7 are graphs illustrating influence curve of moiré patterns obtained based on the luminance curves shown in FIG. 3 and FIG. 5, respectively. With respect to these graphs, the larger the value at a certain angle or position is, the worse the moiré pattern at the angle or the position is, and thus the worse the quality of the display panel is.

Figure 8:
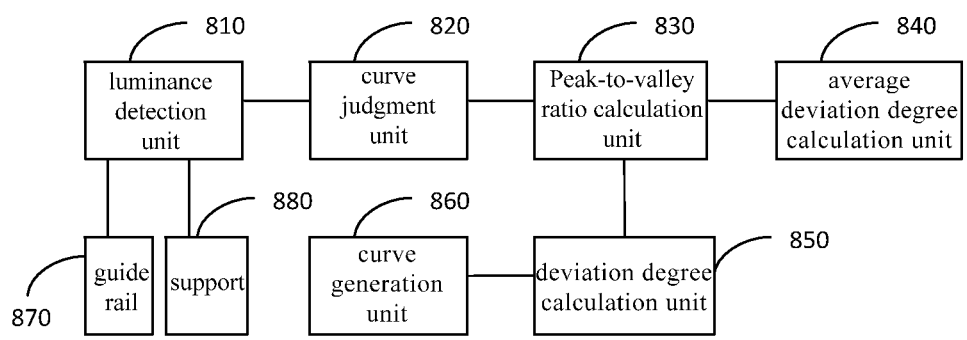
FIG. 8 is a structural schematic diagram of a detection-evaluation device for moiré pattern according to an embodiment of the present invention.

The present invention also provides detection-evaluation device for moiré pattern, comprising a luminance detection unit 810 and a curve judgment unit 820, as shown in FIG. 8.

The luminance detection unit 810 is used for detecting luminances at a plurality of continuous positions in a predetermined region of a display panel which is displaying a full white picture, so as to obtain a luminance curve (which may a virtual luminance curve therein). The luminance detection unit 810 may be a luminance meter or a CCD. The luminance detection unit 810 transmits the luminance curve to the curve judgment unit 820.

The curve judgment unit 820 is used for judging whether a graphics including peaks and valleys exists in the luminance curve, and if the graphics exists, existence of moiré pattern is determined. The curve judgment unit 820 may be a separated processing chip (such as FPGA), and judges whether a graphics including peaks and valleys exists in the luminance curve based on the luminance values on the luminance curve after acquiring the luminance curve. Alternatively, the curve judgment unit 820 may be a processing chip which is integrated into the luminance meter or CCD.

In order to verify the viewing conditions at various view angles (that is, angles within the coverage of view angle of the display panel), the detection-evaluation device for moiré pattern further comprises a support 880 for fixing the luminance detection unit 810 and enabling the luminance detection unit 810 to rotate around a fixed point. The luminance detection unit 810 rotates on the support 880 to continuously detect the luminances at a plurality of different continuous positions on the display panel 200. Specifically, the luminances at the plurality of different continuous positions on the display panel 200 which is displaying a full white picture may be detected through horizontally rotating the luminance detection unit 810 at various detecting angles corresponding to the plurality of different continuous positions horizontally arranged on the display panel (that is, the luminance detection unit 810 rotates in a horizontal plane), and a horizontal luminance curve is obtained, then the existence of moiré pattern is determined based on the horizontal luminance curve. Also, the luminances at a plurality of different continuous positions on the display panel which is displaying a full white picture may be detected at various detecting angles corresponding to the plurality of different continuous positions vertically arranged on the display panel (that is, the luminance detection unit 810 rotates in a vertical plane), and a vertical luminance curve is obtained, then existence of moiré pattern is determined based on the vertical luminance curve. In addition, it is possible to detect horizontally and vertically to obtain two luminance curves. Of course, an oblique detection is also possible, thus a plurality of luminance curves may be obtained to perform a comprehensive detection and evaluation The detection-evaluation device for moiré pattern further comprises a linear guide rail 870 for guiding the luminance detection unit 810 to move along various directions of the display panel. The luminance detection unit 810 performs detections in a manner of linearly translating along the guide rail 300. Preferably, the guide rail 300 is provided parallel to the display panel, and further preferably, the luminance detection unit 810 performs detection of luminance perpendicular to the display panel while linearly translating along the guide rail 300.

Moiré pattern is alternate bright and dark stripes, in a case where moiré pattern is displayed, a graphics including peaks and valleys must be existed in the luminance curve, and in a case where moiré pattern is not displayed, the luminance curve is a uniform arc with high portion in middle and low portions in both ends. In view of above, whether the moiré pattern is displayed may be judged through determining whether the pattern including peaks and valleys exists in the luminance curve. Moreover, according to the positions of peaks and valleys in the luminance curve, the inspection angles at which the moiré pattern can be inspected and the approximate region in the display panel in which the moiré pattern exists can be determined.

In order to further analyse the moiré pattern to evaluate the severity of the moiré pattern displayed on the display panel, the detection-evaluation device for moiré pattern further comprises a peak-to-valley ratio calculation unit 830 and an average deviation degree calculation unit 840 which are connected to each other.

The peak-to-valley ratio calculation unit 830 is connected to the curve judgment unit for calculating a luminance ratio between adjacent peak and valley to obtain several peak-to-valley ratios $P_i$.

The average deviation degree calculation unit 840 is used for calculating an average deviation degree S, with respect to 1, of the peak-to-valley ratios to evaluate the moiré pattern according to the following formula:

$$S = \sqrt{\frac{1}{n-1}\sum_{i=1}^{n}(P_i - 1)^2}$$

where n is the number of the peak-to-valley ratios and $P_i$ is the i-th peak-to-valley ratio. The larger the average deviation degree S is, the worse the moiré pattern is, and thus the worse the quality of the display is.

In the present embodiment, the severity of the moiré pattern may also be judged in another manner, the detection-evaluation device for moiré pattern further comprises a deviation degree calculation unit 850 and a curve generation unit 860 which are connected to each other.

The deviation degree calculation unit 850 is connected to the peak-to-valley ratio calculation unit 830, and is used for calculating deviation degree $s_i = P_i - 1$, with respect to 1, of every peak-to-valley ratio, wherein $P_i$ is the i-th peak-to-valley ratio.

The curve generation unit 860 is used for generating a curve with using angles of detections or the moving distances of detecting points on the display panel as abscissa and using $s_i$ as ordinates. FIG. 6 and FIG. 7 are graphs illustrating influence curve of moiré patterns obtained based on the luminance curves shown in FIG. 3 and FIG. 5, respectively. With respect to these graphs, the larger the value at a certain angle or position is, the worse the moiré pattern at the angle or the position is, and thus the worse the quality of the display panel is.

Each of the above peak-to-valley ratio calculation unit 830, average deviation degree calculation unit 840, deviation degree calculation unit 850 and curve generation unit 860 may be a separated processing chip (such as FPGA) with corresponding function, or may be a separated computer.

In comparison with the conventional visual inspection, an effective and accurate detection for moiré pattern can be realized by adopting the detection-evaluation device for moiré pattern of the present embodiment.

The forgoing embodiments are merely used for illustrating the present invention, but not to limit the present invention. Persons skilled in the art can make various modifications and improvements without departing from the spirit and scope of the present invention, and these modifications and improvements should be considered to be within the protection scope of the present invention. Accordingly, the protection scope of the invention is defined by appended claims.

The invention claimed is:

1. A detection-evaluation method for moiré pattern, comprising:
   step S1, detecting luminances at a plurality of continuous positions in a predetermined region of a display panel which is displaying a full white picture, so as to obtain a luminance curve; and
   step S2, judging whether a graphics including peaks and valleys exists in the luminance curve, and if the graphics exists, determining that there exists moiré pattern;
   wherein after the step S2 the method further comprises:
   calculating a luminance ratio between adjacent peak and valley to obtain several peak-to-valley ratios $P_i$;
   calculating an average deviation degree S, with respect to 1, of the peak-to-valley ratios to evaluate the moiré pattern according to the following formula:

$$S = \sqrt{\frac{1}{n-1}\sum_{i=1}^{n}(P_i - 1)^2}$$

where n is the number of the peak-valley ratios and $P_i$ is the i-th peak-to-valley ratio.

2. The detection-evaluation method for moiré pattern according to claim 1, wherein the step S1 further comprises:
   detecting the luminances at the plurality of continuous positions vertically in a rectilinear direction parallel to the display panel.

3. The detection-evaluation method for moiré pattern according to claim 1, wherein the step S1 further comprises:
   detecting luminances at a plurality of horizontal continuous positions at a reference point to obtain a horizontal luminance curve, and
   detecting luminances at a plurality of vertical continuous positions at a reference point to obtain a vertical luminance curve.

4. The detection-evaluation method for moiré pattern according to claim 1, wherein the detection in the step S1 is performed by using a luminance meter or a CCD.

5. A detection-evaluation method for moiré pattern, comprising:
   step S1, detecting luminances at a plurality of continuous positions in a predetermined region of a display panel which is displaying a full white picture, so as to obtain a luminance curve; and
   step S2, judging whether a graphics including peaks and valleys exists in the luminance curve, and if the graphics exists, determining that there exists moiré pattern, wherein after the step S2, the method further comprises:

calculating a luminance ratio between adjacent peak and valley to obtain several peak-to-valley ratios $P_i$;

calculating a deviation degree $s_i=P_i-1$, with respect to 1, of every peak-to-valley ratio, wherein $P_i$ is the i-th peak-to-valley ratio; and generating a curve with using angles of detections as abscissa and using $s_i$ as ordinates so as to evaluate the moiré pattern.

6. A detection-evaluation device for moiré pattern, comprising:

a luminance detection unit which is used for detecting luminances at a plurality of continuous positions in a predetermined region of a display panel which is displaying a full white picture, so as to obtain a luminance curve; and a curve judgment unit which is used for judging whether a graphics including peaks and valleys exists in the luminance curve, and if the graphics exists, the curve judgment unit determines that there exists moiré pattern, wherein the detection-evaluation device further comprises:

a peak-to-valley ratio calculation unit which is used for calculating a luminance ratio between every adjacent peak and valley to obtain several peak-to-valley ratios $P_i$;

an average deviation degree calculation unit which is used for calculating an average deviation degree S, with respect to 1, of the peak-to-valley ratios to evaluate the moiré pattern according to the following formula:

$$S = \sqrt{\frac{1}{n-1}\sum_{i=1}^{n}(P_i-1)^2}$$

where n is the number of the peak-valley ratios and $P_i$ is the i-th peak-to-valley ratio.

7. The detection-evaluation device for moiré pattern according to claim 6, further comprising a linear guide rail which is parallel to the display panel, and wherein the luminance detection units moves along the linear guide rail.

8. The detection-evaluation device for moiré pattern according to claim 7, wherein the luminance detection unit vertically detects a luminance at each of the continuous positions to obtain a luminance curve.

9. The detection-evaluation device for moiré pattern according to claim 6, further comprising a support for fixing the luminance detection unit and enabling the luminance detection unit to rotate around a fixed point, so that luminances at a plurality of horizontal continuous positions are detected by the luminance detection unit, so as to obtain a horizontal luminance curve, and luminances at a plurality of vertical continuous positions are detected by the luminance detection unit, so as to obtain a vertical luminance curve.

10. The detection-evaluation device for moiré pattern according to claim 6, the luminance detection unit includes a luminance meter or a CCD.

11. The detection-evaluation device for moiré pattern according to claim 7, further comprising:

a peak-to-valley ratio calculation unit which is used for calculating a luminance ratio between every adjacent peak and valley to obtain several peak-to-valley ratios $P_i$;

an average deviation degree calculation unit which is used for calculating an average deviation degree S, with respect to 1, of the peak-to-valley ratios to evaluate the moiré pattern according to the following formula:

$$S = \sqrt{\frac{1}{n-1}\sum_{i=1}^{n}(P_i-1)^2}$$

where n is the number of the peak-valley ratios and $P_i$ is the i-th peak-to-valley ratio.

12. A detection-evaluation device for moiré pattern, comprising:

a luminance detection unit which is used for detecting luminances at a plurality of continuous positions in a predetermined region of a display panel which is displaying a full white picture, so as to obtain a luminance curve; and a curve judgment unit which is used for judging whether a graphics including peaks and valleys exists in the luminance curve, and if the graphics exists, the curve judgment unit determines that there exists moiré pattern, wherein the detection-evaluation device further comprises:

a peak-to-valley ratio calculation unit which is used for calculating a luminance ratio between adjacent peak and valley to obtain several peak-to-valley ratios $P_i$;

an average deviation degree calculation unit which is used for calculating a deviation degree $s_i=P_i-1$, with respect to 1, of every peak-to-valley ratio, wherein $P_i$ is the i-th peak-to-valley ratio; and a curve generation unit which is used for generating a curve with using angles of detections as abscissa and using $s_i$ as ordinates so as to evaluate the moiré pattern.

13. The detection-evaluation method for moiré pattern according to claim 1, wherein the step S1 further comprises:

detecting luminances at a plurality of horizontal continuous positions at a reference point to obtain a horizontal luminance curve, or detecting luminances at a plurality of vertical continuous positions at a reference point to obtain a vertical luminance curve.

14. The detection-evaluation device for moiré pattern according to claim 6, further comprising a support for fixing the luminance detection unit and enabling the luminance detection unit to rotate around a fixed point, so that luminances at a plurality of horizontal continuous positions are detected by the luminance detection unit, so as to obtain a horizontal luminance curve, or luminances at a plurality of vertical continuous positions are detected by the luminance detection unit, so as to obtain a vertical luminance curve.

* * * * *